United States Patent [19]

Smith

[11] Patent Number: 5,587,396
[45] Date of Patent: Dec. 24, 1996

[54] METHOD OF AMELIORATING CELLULITE BY DISRUPTING THE BARRIER FUNCTION OF THE STRATUM CORNEUM

[75] Inventor: Walter P. Smith, New Canaan, Conn.

[73] Assignee: Mary Kay Inc., Dallas, Tex.

[21] Appl. No.: 296,513

[22] Filed: Aug. 26, 1994

[51] Int. Cl.⁶ .................................................. A61K 31/19
[52] U.S. Cl. ........................ 514/557; 514/558; 514/559; 514/563; 514/725
[58] Field of Search .................................... 424/401, 451, 424/195.1, 489; 128/243, 65, 57

[56] References Cited

U.S. PATENT DOCUMENTS

| | | | |
|---|---|---|---|
| 4,086,922 | 5/1978 | Henderson | 128/24.3 |
| 4,363,815 | 12/1982 | Yu et al. | 424/274 |
| 4,737,421 | 4/1988 | Uemura et al. | 429/34 |
| 4,829,987 | 5/1989 | Stewart | 128/65 |
| 5,030,451 | 7/1991 | Trebose et al. | 424/401 |
| 5,051,449 | 9/1991 | Kligman | 514/559 |
| 5,091,171 | 2/1992 | Wu et al. | 424/642 |
| 5,190,876 | 3/1993 | Merril, Jr. et al. | 435/240.2 |
| 5,215,759 | 6/1993 | Mausner | 424/489 |
| 5,382,432 | 1/1995 | McCook et al. | 424/401 |

OTHER PUBLICATIONS

J. Pinnagoda, et al., "Measurement of the Transepidermal Water Loss," Chapter 9.1, (1995) pp. 173–178.
Rieger et al. "Skin Constituents as Cosmetic Ingredients" *Cosmetics and Toiletries* v. 107, pp. 85–94 (Nov. 1992').
Merck Index, element edition, Merck & Co., Inc. 1989, monograph number 477.

Proksch et al. "Barrier Function regulates epidermal lipid and DNA synthesis" British Journal of Dermatology (1993) 128, 473–482.

*Primary Examiner*—Gary Geist
*Assistant Examiner*—Deborah D. Carr
*Attorney, Agent, or Firm*—Finnegan, Henderson, Farabow, Garrett & Dunner, L.L.P.

[57] ABSTRACT

New topically applied treatments for cellulite are shown by comparative data to effect structural improvements in cellulite-afflicted thigh area tissues including skin-thickening, thigh-firming and thigh-reduction. The disclosed treatments disrupt the skin's water barrier and elevate trans-epidermal water loss (TEWL) for extended periods of weeks or months and include methods of mechanical or solvent action, for example, tape stripping, or acetone washes. Preferred treatments use creams with active ingredients such as lactic acid to elevate TEWL, a retinoid, preferably vitamin A palmitate to disrupt barrier rebuilding and prolong elevation of TEWL levels, and a cerebroside to inhibit lipid synthesis and intensify the TEWL elevation. Diuretics, for immediate esthetic improvements, anti-irritants and anti-oxidants for irritation control are optional ingredients.

15 Claims, No Drawings

METHOD OF AMELIORATING CELLULITE BY DISRUPTING THE BARRIER FUNCTION OF THE STRATUM CORNEUM

TECHNICAL FIELD

The present invention relates to topically applied cellulite treatments, being compositions and methods which produce structural improvements in cellulite conditions when used on a long-term basis, for example, when applied daily for several months. The term "cellulite" refers to abnormal accumulations of fatty cells in masses beneath the skin which produce unsightly topical and visual discontinuities of the skin surface.

BACKGROUND

Cellulite, a term coined by Nicole Ronsard in the 1970's (see Webster's New Universal Unabridged Dictionary, 2nd ed. Dorset & Baber 1983) describes a widespread condition in which abnormal subcutaneous deposits of irregular fatty masses produce unsightly disturbances in the skin's normally smooth curvatures.

Physiologically, cellulite is caused by a degeneration of the micro circulation in areas of the body prone to fatty deposits. Severe cellulite is characterized by degeneration of subcutaneous blood vessels, poor blood flow, a thinning of the epidermal and dermal layers of the skin, the presence of hard lumps of fatty material surrounded by protein in the subcutaneous regions, and an accumulation and pooling of body fluids. The result in the skin taking on an "orange peel" appearance.

Cellulite is most commonly problematical on the thighs, buttocks and upper arms, less so on the outer limbs, back, torso and midriff and is not usually significant on the face, neck, hands and feet. While often associated with obesity, cellulite may also manifest itself in the skin of individuals of normal or near-normal weight. It is more prevalent on females than males and more apparent on Caucasians than darker skinned individuals.

Detracting greatly from an individual's appearance, cellulite can have profound psychological effects, damaging the self-esteem of many afflicted individuals and perhaps seriously undermining the healthy psychological development of some young women and men. There is, accordingly, a great need for effective cellulite remedies.

Known methodologies for cellulite treatment include localized mechanical action, topical application of chemical agents, exercise, dietary adjustments, and combinations of these therapies. One effective treatment is a combination of diet and exercise, rigorously maintained over an extended period. Many people seek easier remedies. As I have verified, by clinical tests described herein, known easily applied topical treatments provide only superficial benefits and fail to improve structural defects significantly.

Stewart U.S. Pat. No. 4,829,987 teaches a cellulite treatment requiring the application of a mineral-solution-soaked wrap to an appropriate body portion, followed by passive exercise of that body portion. This treatment would be too inconvenient or demanding for many people.

Massage improves microcirculation and stimulates exfoliation, smoothing the skin surface and increasing blood flow, but only temporarily. Henderson U.S. Pat. No. 4,086,922 discloses a massage device and method for treating cellulite. The device comprises multiple resiliently loaded balls that are applied to massage afflicted body areas.

Heat treatment also stimulates microcirculation and may provide temporary benefits, but no long-term structural improvements.

Body lotions, tonics and creams containing supposedly active biologicals, for example, witch hazel, broom, horse chestnut, algae, sea water or escine, may provide temporary, mild microcirculatory stimulation but are at best modestly active.

The aforesaid massage, heat treatment and biological formulations do not address problems of skin renewal, fat catabolism, body fluid accumulation or the regeneration of blood vessels.

Diuretics, (botanicals are usually preferred), promote lymphatic drainage, yielding good short-term symptomatic effects but do not address long-term skin defects, fat catabolism or blood vessel regeneration.

Caffeine, theophylline and other xanthines, appear to be effective, in high concentrations, as diuretics and also in promoting fat catabolism. Aminophylline, currently a popular active ingredient in what are known as thigh creams or thigh-smoothing creams, appears to be effective as a powerful diuretic in promoting lymphatic drainage but is reported to have significant toxic side effects (see The Merck Index eleventh edition, Merck & Co. Inc. 1989 monograph number 477). Such agents do not address underlying structural defects of the skin and blood vessels.

Some cosmetic compositions incorporating modified caffeine derivatives as active agents are described in Trebosc et al. U.S. Pat. No. 5,030,451. According to Trebosc et al., column 9, lines 15–20, the disclosed formulations have "excellent and long-acting 'lipolytic properties' and have therefore proven very effective in slenderizing programs and in the treatment of cellulitis."

However, no efficacy data is reported. At column 1, lines 61–65, Trebosc et al. teach that a faster rate of transcutaneous passage confirms the superiority of these agents in the treatment of cellulite.

Mausner U.S. Pat. No. 5,215,759 references the use of methylsilanol theophyllinacetate alginate and methylsilanol mannuronate for anti-cellulite activity. Lacking explanatory disclosure, the action of these substances is presumably equivalent to diuretics.

One drawback to marketing stimulant compositions (containing caffeine, aminophylline or related agents as active ingredients) for consumer treatment of cellulite, is that drug issues may be raised preventing their being included in cosmetic compositions for over-the-counter sale. Repeated long-term use may induce harmful side effects, and government regulations may limit marketability. Another drawback is that such agents fail to address underlying structural problems of skin and blood vessel defects.

Exfoliating granules act mechanically, abrading the outer layers of the skin, smoothing the skin surface and promoting skin renewal, but fail to promote lymphatic drainage, long-term microcirculatory regeneration or fat catabolism. Exfoliating granules are hard particles, generally suspended creams or gels, that are rubbed or massaged on the skin to achieve a mechanical exfoliation. The granules are usually polyethylene spheres, however natural particles like peach or apricot crushed pits have been used. A further drawback of these products is that it is hard to control irritation.

Topically applied retinoids, for example, as disclosed in Kligman U.S. Pat. No. 5,051,449, can ameliorate cellulite to a limited extent. Kligman gives qualitative reports of comparative benefits obtained after more than six months of topical applications of a retinoic acid preparation, versus an unidentified non-medicated "purpose" cream. These benefits are described as including skin thickening, an increase in the number of new blood vessels, and an observable moderate-to-marked improvement (of cellulite) using a pinch test (column 6, lines 50–61). No quantitative data are given so that the value of Kligman's teaching for treating cellulite cannot be determined by one skilled in the art.

Many people want and expect greater efficacy from a cellulite treatment than is provided by moderate improvements after six months of treatment. Applied concentrations of retinoic acids must be limited to avoid inducing irritation (see Kligman column 2, lines 59–60), so that adequate efficacy cannot be achieved by increased dosages. Thus retinoic acid treatments do not provide a satisfactory long-term treatment for cellulite and there is a need for more effective topical treatments. In contrast to Kligman's unsubstantiated generalizations, I have found in quantified clinical studies that retinoic acid provides no significant skin thickening after three months of daily treatments. Accordingly, there is a need for an easily applied cellulite treatment which provides structural improvements in a reasonable period of time.

SUMMARY OF THE INVENTION

The invention, as claimed, is intended to provide a remedy. It solves the problem of providing a consumer-marketable, easily applied topical cellulite treatment that has greater efficacy than has heretofore been obtainable, and that effects significant structural improvements in a reasonable period of time. The invention also solves the problem of providing a topical cellulite treatment which yields progressive, structural improvements when continually applied long term. Preferred embodiments promote significant thickening of the skin in cellulite-afflicted areas of the body along with improvements in tissue firmness reductions in thigh diameter and increased microcirculatory blood flow.

The invention solves the above-described problem by providing a cellulite treatment method which obtains enhanced efficacy by disrupting the water barrier properties of the skin in areas overlying cellulite-afflicted tissues for a sustained period of time long enough to provoke substantial skin renewal and regeneration of blood vessels.

There are difficulties in disrupting the skin barrier in a sustained manner. Obviously, the disruption process must not be so severe as to damage the sensitive dermal layers of the skin or to cause pain or significant irritation. Yet to obtain the benefits of my invention, the treatment should provide more than a transitory effect, with a lasting disruption of barrier function. Because proper functioning of the barrier is so essential to survival, disruption of the barrier sets in motion natural processes that act rapidly to repair the barrier. More specifically, barrier function should continue to be disrupted during an extended treatment period of weeks, for example eight weeks or more. Elevation of trans-epidermal water loss can be used to monitor barrier function. When TEWL levels are measured after twelve weeks of treatment, taking measurements at least eight hours after application of the last treatment, I have found that known cellulite treatments, other than retinoids have little, if any, sustained impact on barrier function and some appear to depress TEWL levels. Retinoic acid, an exfoliant, and at least one other exfoliant, show only marginal elevations of TEWL at twelve weeks.

Notwithstanding these difficulties, I have found a diversity of treatments that are effective to disrupt barrier function and which when applied continually over an extended period, for example daily or twice daily, produce significant increases of TEWL at eight weeks or twelve weeks.

Some barrier disruption treatments that can be used in the practice of this invention include direct physico-chemical destruction of the lipid structure of the stratum corneum by a dermatologically tolerable organic solvent for low molecular weight non-polar lipids, such as acetone or by a dermatologically tolerably surfactant, for example sodium lauryl sulfate. Such treatments detach and remove barrier-component lipids. Preferred, however, is the use of a topically applied cosmetic composition, containing chemically active barrier disruption ingredients in an aesthetically attractive, non-odorous formulation such as a cream for absorption into the skin. Other suitable barrier disruption treatments will be known or apparent to those skilled in the art.

I have further discovered that by inhibiting synthesis of skin lipids, repair of the barrier can be inhibited or controlled and the elevation of long-term eight- or twelve-week TEWL levels can be substantially intensified. As taught by Proksch et al. in "Barrier function regulates epidermal lipid and DNA synthesis" British Journal of Dermatology (1993) 128, 473–482, murine studies show that disruption of barrier function results in an increase in the synthesis of free fatty acids, sphingolipids and cholesterol in the living layers of the epidermis, leading to barrier repair.

In optional embodiments of this invention, such synthesis is inhibited to reduce the availability of free fatty acids, sphingolipids and cholesterol to repair the water barrier, for example by topical application of a cerebroside for absorption. Other suitable inhibitors will be known or apparent to those skilled in the art. Where the cellulite treatment removes or washes away skin lipids, the lipid synthesis inhibitor is applied in a separate step from barrier disruption. Where barrier disruption is effected by topically absorbed active agents, a lipid synthesis inhibitor can be included in the formulation.

Such use of a lipid synthesis inhibitor can prevent rapid regeneration of the water barrier and provide enhanced structural improvements in cellulite conditions.

I have also discovered that trans-epidermal water loss (TEWL (which is susceptible to direct measurement)), when considered over the full course of an extended long-term cellulite treatment of eight weeks or more, is a valuable parameter for monitoring the efficacy of cellulite treatments. The degree of elevation of TEWL achieved on a sustained basis is also a useful predictor of the efficiency of cellulite treatments whose benefits only become evident in the long-term, after weeks or, more probably two to six months or more of use. By making TEWL measurements on the subjects of a variety of cellulite treatments, which measurements I believe have not heretofore been used to assess the merits of cellulite therapies, I have found that known treatments offer only temporary, short-lived elevation of TEWL and none provides a sustained elevation of TEWL over weeks or months. I have found that by provoking substantial and sustained elevation of TEWL, valuable structural improvements in cellulite conditions can be obtained.

Furthermore, by monitoring TEWL levels induced by various treatments, I have been able to devise new treatments for cellulite which are effective to sustain chronically or continually elevated TEWL levels throughout a treatment period typically lasting eight weeks, twelve weeks or more. Preferably my new treatments elevate TEWL by at least one hundred percent for extended periods of eight weeks or more. Substantially higher elevations of two or three hundred percent or more, throughout the treatment period are desirable.

In one aspect, the invention provides a method of ameliorating a cellulite condition which comprises continually applying a topical water-barrier disruption treatment to overlying skin areas to induce chronic elevated trans-epidermal water loss for a period of from eight weeks until a desired amelioration of cellulite is achieved. Typically the treatment is applied once or twice a day.

My new cellulite treatments include various topical mechanical treatments of the skin, for example abrading, roughening or stripping and solvent extraction treatments, both of which treatments are to be carried out sufficiently vigorously or aggressively to elevate TEWL levels by one hundred percent or more, as mentioned above, and are to be sustained for extended periods. However, a preferred treatment comprises a chemical composition that can be topically applied, preferably in an emollient or cream formulation, and sustains elevated TEWL levels with applications that are no more frequent than once or twice a day.

Clearly the aggressiveness of the inventive treatments must be controlled to be tolerable over periods of weeks or months without causing severe or painful irritation, reddening, peeling or excessive discomfort. However, minor manifestations of these symptoms may be tolerable by many people for short periods of time.

In another aspect the invention provides a cellulite treatment composition which comprises a TEWL elevator that is effective to raise immediate or short-term TEWL levels accompanied by a barrier disruption agent that functions to sustain the elevated TEWL levels. Preferably, the composition includes a cell renewal/differentiation modulater to sustain the skin repair processes. Preferably also, a skin lipid synthesis inhibitor is included in the composition to prevent premature rebuilding of the water barrier and enhance the composition's cellulite treatment efficacy.

In a preferred embodiment of this aspect of the invention the TEWL elevator is a cosmetically compatible, pH-reducing, hydroxycarboxylic acid, preferably with exfoliant properties, and is at least moderately soluble in water or a hydroalcoholic vehicle for incorporation into cosmetic composition. Such acids include alpha hydroxycarboxylic acids, especially for example, lactic acid and glycolic acid, as well as other hydroxycarboxylic acids, for example 2-hydroxybenzoic acids, especially for example, salicylic acid. The effectiveness of such acids appears to relate to their ability to reduce the pH of intercellular fluids in the skin. A particular acid to use, and its concentration are selected to obtain a desired TEWL elevation without excessive irritation.

A preferred barrier repair inhibitor is a retinoic acid or a derivative thereof, one particularly preferred retinoic acid being vitamin A palmitate. Clinical tests I have conducted, involving in vivo studies of human responses to diverse cellulite treatments, details of which are reported below, show a quite unexpected beneficial interaction between lactic acid and vitamin A palmitate which is valuable in the long-term treatment of cellulite.

A preferred lipid synthesis inhibitor is a cerebroside or a cerebroside-rich material. Some optional ingredients are diuretics to stimulate blood flow and remove excess liquids, and anti-irritants to moderate irritant side effects of the TEWL elevator or cell renewal stimulant.

Suitable relative proportions for formulating the ingredients of the inventive compositions as topical applications for sale in cosmetic or medicament emollient, lotion or tonic formulations, and their application rates, are described hereinbelow. A preferred cosmetic formulation is a cream suitable for daily massaging, or simply spreading 26 and rubbing, by the consumer. Other such quantitative parameters that can be used to obtain the benefits of this invention will be apparent to those skilled in the art.

As experimental data described hereinbelow shows, compositions according to the invention provide new levels of effectiveness in treating cellulite and are capable of significantly increasing skin thickness, improving blood flow and promoting angiogenesis. As reported, these and other product efficacy characteristics are carefully quantified.

Cellulite areas have defective blood flow. Clinical tests with embodiments of the invention, reported hereinbelow, showed immediately improved blood flow for 4–8 hours and with chronic use, for 8–16 weeks, long-term blood flow was improved through angiogenic effects, thus reducing the defects in the cellulite afflicted tissues. Furthermore, skin thickness was increased in the epidermal-dermal skin region and skin density was increased in the subcutaneous region, after 8 to 16 weeks of treatment. More importantly, tissue density was improved indicating this was a positive effect and that the dermis and epidermis were more firm and elastic and the subcutaneous regions had less fat and would have reduced extraneous fluid. These are structural improvements attributable to the inventive treatments.

DETAILED DESCRIPTION OF THE PREFERRED EMBODIMENTS

Cellulite Described

The pathogenesis of cellulite is usually described as a three-or-four-stage process. Herein, cellulite pathogenesis will, for the purposes of providing an explanatory model, without limiting the scope of the invention, be considered as a three-stage process having the following characteristics:

Stage 1

Blood vessels in the affected area become dilated and leaky. At this stage, surface effects are minimal and treatments to repair vascular integrity and remove excess fluid can be quite effective. Laser Doppler examination can detect abnormal blood flow and biopsies also show sub-surface defects.

Stage 2

Fat cell metabolism is grossly disturbed with a dramatic increases in the amount of fat and size of cells. Fat globules form as engorged fat cells adhere together. Vascular integrity is further impaired, dermal and epidermal disturbances are noted. Examples of such disturbances are epidermal thinning, poor vasculature in the dermis, the skin surface becoming rough and gray due to poor micro-circulation and surface heterogeneity develops, i.e. the beginnings of an "orange-peel" surface can be seen.

Stage 3

In the third stage, a continued breakdown of the microvasculature can be observed, with continued fluid accumulation, increasing fat synthesis and decreasing rates of fat metabolism. Fat cells are engorged, adhere together and are surrounded by a collagen shell, made up of abnormal collagen. These distinct nodules can be several centimeters in diameter, are quite palpable at the surface, and may be quite painful. The collagen-shelled fat nodules re-direct the capillary network and represent areas where blood flow is diminished. The subcutaneous fat region is quite disorganized from fluid retention, from the presence of fatty nodules and from the effects of gravity. The orange peel skin is readily apparent, surface heterogeneity is obvious. The epidermis and dermis are thinner and less firm and organized. The abnormalities can be readily detected visually at the skin surface and are unsightly and embarrassing to most people afflicted with advanced cellulite.

Cellulite Determinations

A number of biophysical techniques are available for measuring and documenting cellulite, for example, firmness and elasticity can be measured directly, via laser Doppler blood flow, via thermography, and of course with historical evaluations. Various of these techniques may be appropriate for determining the effectiveness of a particular cellulite treatment, depending upon the symptoms addressed by the treatment. Some additional techniques have been developed for improved clinical evaluation of the cellulite treatment methods and compositions described herein. There follows a short, non-exhaustive listing of such treatments:

Thigh diameter measurements

Track the effectiveness of products that act to thin cellulite areas. Works best with regimens involving diet and exercise. This is a poor, insensitive and indiscriminate method.

Laser Doppler measurements

Can detect breakdowns in the vasculature, and the effects of a product on vasculature integrity. Short-term vasodilation induced by a product can be easily seen. Longer-term observation of angiogenic (blood vessel generation) effects and vascular integrity, produced by better products, can be monitored but is more difficult and requires good technical expertise.

Ultrasound scans

Are a very effective technique, detecting changes in subcutaneous fat, blood vessel distribution and epidermal and dermal integrity. Skin thickness can be measured by a computer analysis of skin ultrasound scans. Ultrasound scans provide a non-invasive way to make objective and accurate determinations of epidermal and dermal thickness.

Thermography

A more graphic way than laser Doppler to demonstrate blood vessel insufficiencies.

Skin firmness and elasticity

Measures the general health and integrity of the entire dermis, epidermis and subcutaneous regions.

Cellulite grading

The cellulite grading data reported hereinbelow are aggregate numbers representing the results of a visual inspection of the skin for lumpiness, sagging of the skin and surface defects as well as pinching the skin to access nodules.

Histology

Histology (examination of skin biopsies) can show changes like measures in collagen and elastin synthesis, production of new blood vessels and can document structural changes. Histology is usually the most accurate way to describe the extent of a cellulite problem and to determine the real effects of a product, but is invasive and has other drawbacks.

Photography & Replicas

These are of limited value. Consumer impressions are often a better tool. Cellulite is a "macro" surface effect and replicas often show too much detail. Photography is difficult to evaluate.

PREFERRED EMBODIMENTS OF THE INVENTION

Preferred embodiments of this invention employ methods or materials that provoke a loss of skin water-barrier function to induce the release of factors in the skin that, in essence initiate a skin repair process. By disrupting barrier function, the skin responds as though wounded and begins a generalized repair process increasing epidermal and dermal metabolism and angiogenesis, or blood vessel formation, under the control of as yet undefined skin signals released upon barrier disruption.

Observations made during the course of developing the data reported hereinbelow, suggest that massage, the use of abrasive sponges (BUFF-PUFF (trademark)), and exfoliative granules, although they may temporarily increase TEWL, for a few minutes or hours after application, do not sustain such effects. From these observations, I have postulated that chronic elevated TEWL is necessary to achieve desired structural improvements.

Similarly, exfoliant treatments such as facial peels (for example, 20–30% lactic or glycolic acid or equivalent), in single applications, or repeated at intervals, such as weekly, although they increase TEWL for several days after treatment, do not achieve the desired skin repair and cellulite improvement effects. Again, pursuant to the concepts of this invention, these deficiencies are believed to be due to a failure of the treatment to provide a sustained elevated rate of TEWL over an extended course of treatment, for example, lasting at least eight weeks.

Experimental data described hereinbelow demonstrate that no previously known cellulite treatment produces a sustained disruption of barrier function and none produces sufficiently significant effects to hold the promise of restoring areas afflicted with advanced cellulite to a normal or near-normal condition by means of an easily applied topical, local treatment.

TEWL Determinations

Pursuant to the present invention, TEWL measurements were made on subjects of various cellulite treatments including both conventional treatments and novel treatments some of which are according to the present invention. Basal blood flow determinations, thigh diameter measurements and comparative clinical gradings of cellulite, and of induced irritation, were also made.

A SERVO-MED brand evaporimeter was used for TEWL determinations. This equipment comprises a moisture-collection chamber which occludes a skin surface area. The instrument detects moisture-dependent conductance and TEWL levels are read when steady state conditions are reached. Subjects are pre-conditioned at a temperature of about 68°–71° C. of and a relative humidity of about 30–40%. The instrument employed for the tests described below had a sensitivity of about ±10%.

In the clinical experiments reported below, protocols involving determination of TEWL levels at skin areas receiving topically applied cellulite treatments employed a procedure in which a cellulite or other comparative topical treatment was applied twice daily and a TEWL determination was made a short time prior to a morning application. For example, in many cases, the treatment was applied at about 10 a.m. and about 6 to 8 p.m. while the TEWL determination was made about 9 a.m., approximately one hour prior to the morning application and at least eight, or more probably twelve, hours after the evening application.

A number of prior art cellulite treatments were evaluated for their efficacy in elevating TEWL levels, using the method described in the preceding paragraph. Basal blood flow was evaluated using laser Doppler determinations and then rated on a comparative scale. In addition, thigh firmness and diameter were determined by methods known to those skilled in the art and skin thickness was determined by ultra sound as described above. Skin thickness was determined for the epidermal-dermal layers, first figure and also for the subcutaneous region, second figure in parenthesis. As the skin structure improves with treatment, the epidermal-dermal layers thicken (increases in the first figure) and the soft, liquid-bearing subcutaneous region decreases (negative figure in parenthesis) as improved microcirculation removes excess liquids. Cellulite severity was clinically rated on comparative scale, as was irritation.

In the following clinical experiments a cellulite grading was determined according to the following scale:

0 No surface unevenness or defects.

Body Contouring Gel" which increased skin surface temperature via a chemical reaction.

Exfoliation for treatment 1.5 was a mechanical exfoliation with 5% polyethylene beads suspended in a carbopol gel, vigorously applied and rinsed off twice a day.

Vasoactive herbs for treatment 1.6 were a commercial product from Orlane under the trade name "Rhythme Du Corps".

TABLE 1

Evaluation of Conventional Cellulite Treatments

| Treatment | Blood flow | TEWL g/m2/hr | Firm-ness | Thigh Diam. | Skin Thickness | Cell. Grade | Irrit. Grade |
|---|---|---|---|---|---|---|---|
| 1.1) RETIN A* 0.5% | | | | | | | |
| baseline | 1 | 2.17 | x | x | x | 4 | 1 |
| 8 wks | x | x | x | x | x | 4 | 2 |
| 12 wks | 1.27 | 2.37 | 32% | −8% | 4%(ns) | 3 | 2.5 |
| 1.2) massage | | | | | | | |
| baseline | 1 | 2.41 | x | x | x | 4 | 1 |
| 8 wks | x | x | x | x | x | 4 | 1 |
| 12 wks | 0.97 | 1.97 | 6% | −2% | ns(ns) | 4 | 1.25 |
| 1.3) caffeine/theophylline | | | | | | | |
| baseline | 1 | 2.33 | x | x | x | 4 | 1 |
| 8 wks | x | x | x | x | x | 4 | 1 |
| 12 wks | 1.08 | 2.47 | −3% | −3% | 2%(ns) | 3.75 | 1.25 |
| 1.4) heat/xanthines | | | | | | | |
| baseline | 1 | 2.61 | x | x | x | 4.25 | 1 |
| 8 wks | x | x | x | x | x | 4.25 | 1.25 |
| 12 wks | 1.03 | 2.23 | 4% | −5% | ns(−2%) | 4 | 2 |
| 1.5) exfoliation | | | | | | | |
| baseline | 1 | 2.41 | x | x | x | 4.25 | 1 |
| 8 wks | x | x | x | x | x | 4 | 1.5 |
| 12 wks | 1.07 | 2.17 | 13% | −3% | ns(−3%) | 4 | 2.25 |
| 1.6) vasoactive herbs | | | | | | | |
| baseline | 1 | 2.23 | x | x | x | 4.25 | 1 |
| 8 wks | x | x | x | x | x | 3.75 | 1.25 |
| 12 wks | 1.01 | 2.41 | 7% | 1% | ns(−3%) | 3.75 | 1.5 |

* Trademark of Johnson & Johnson Co. for retinoic acid. ns = not significant

1 Visible discrete depressions on surface or dimples.

2 Visible larger linear striations (depressions on surface).

3 Multiple visible and palpable striations and depressions, uneven skin tone, color variation.

4 As in for grade 3 with palpable sub-surface nodules.

Irritation was evaluated by comparative chromaticity determinations of skin color, by industry standard methods, employing a Minolta Chroma Meter, Minolta Camera Co. Ltd. Additional subjective perceptions of stinging, burning and skin redness after application were recorded, and the data were combined into a clinical irritation index having a scale of from 0 to 5 on which 0 indicates no discernible or reported irritation, and 5 indicates severe irritation.

Clinical Experiments with Prior Art Cellulite Treatments

The results of clinical experiments with prior art cellulite treatments are reported in Table 1 below. The prior art actives in Table 1 were all applied twice a day for the duration of the study.

For treatment 1.1 Retin A (trademark) was supplied at a concentration of 0.5% in a simple cream base.

Massage for treatment 1.2 was done by hand and with a mechanical implement using olive oil as a massage oil.

Caffeine and theophylline for treatment 1.3 were at concentrations of 2% and 0.2% respectively in a simple gel.

Treatment 1.4 applying heat and xanthines employed a product from La Prairie having the trade name "Cellular The first five columns of results were analyzed for statistical significance with the result that only the 12-week data for blood flow, firmness and thigh diameter of treatment 1.1 were rated as significant. (Clinical gradings of cellulite severity and irritation in columns 6 and 7 are subjective and not subject to statistical analysis.)

Referring to the data, only treatment 1.1 with retinoic acid shows any significant improvement in basal blood flow, while treatments 1.3, caffeine and 1.5, exfoliation show slight, but not significant elevations of blood flow.

Referring to the TEWL levels in Table 5 and comparing the levels at twelve weeks with the baseline levels, it can be seen that little, if any, significant elevation is achieved with any of the prior art cellulite treatments, even at twelve weeks. Treatment 1.1, using retinoic acid, shows the best prior art elevation but this was barely 10%. As will be described inventive treatments can attain blood flow elevations in excess of 40%.

Thigh firmness and diameter are marginally improved by treatment 1.5, exfoliation, and more significantly improved by treatment 1.1, retinoic acid. Substantially more significant improvements are obtained with the present invention.

Only very modest, or insignificant, improvements in skin thickness were shown by the prior art cellulite treatments of Table 1.

Treatment 1.1, retinoic acid, showed some general reduction in cellulite severity, as clinically graded but at a cost of a substantial increase in irritation, as reported in the last two columns of Table 1.

These data show that known cellulite treatments provide only modest benefits, with the best results being obtained with retinoic acid, followed by exfoliation. Some improvements in basal blood flow, firmness, thigh diameter and general cellulite condition are obtained, at the cost of significant irritation. Neither significant elevation of TEWL nor improvement in skin thickness, a fundamental structural indicator of tissue health, was obtained with prior art treatments, clearly showing the shortcomings of the prior art. Although the invention is not limited by any particular theory, it appears that no prior art treatment provides a sufficiently sustained disruption of the skin's water barrier function to stimulate significant skin repair.

Novel Cellulite Treatments

As stated above, the present invention provides a method of topical treatment for cellulite which decreases skin water barrier function, preferably with a 200 to 300 percent increase, or greater, in TEWL, continually and chronically over at least 8 week period and preferably beyond that period to 26 weeks or such other time as a satisfactory improvement in the cellulite condition is obtained, for example 10 to 20 weeks.

The desired TEWL increases can be obtained by sustained treatments with suitable chemical compositions or mechanical disruptions or solvent extraction, provided the treatments are sufficiently aggressive to disrupt the skin water barrier. Important to the invention is to increase TEWL while maintaining a low, tolerable, irritation level since caustic chemicals used to disrupt the barrier, solvents used to extract lipids, and surfactants can all be very irritating.

In practicing a particularly preferred embodiment of this invention, I have discovered that a combination of unbuffered lactic acid, an example of an alpha hydroxy acid, used at relatively strong concentrations, together with vitamin A palmitate or alcohol, synergistically increases TEWL. The alpha hydroxy acid disrupts the skin's water barrier and acts as a TEWL elevator. It appears that vitamin A palmitate, a retinoid, inhibits restoration of barrier functions and delays a return of TEWL levels which have been elevated by alpha hydroxy acid treatment. These TEWL-stimulating properties may be attributable to the effects of retinoids on skin cell differentiation. This interaction of vitamin A palmitate with lactic acid is quite unexpected.

Preferred embodiments of the invention when applied topically to the skin are believed to chronologically and severely exfoliate the skin so as to induce extensive cell loss and more importantly disrupt normal barrier functions so that TEWL is increased preferably as much as 200 to 300 percent. Although physical means can be used to achieve these effects, it is a discovery of this invention that between 5–10% unbuffered lactic acid and 0.1%–3.0% vitamin A palmitate achieves this result reproducibly with modest irritation. A combination of 6% lactic acid and 0.5% vitamin A palmitate, was found to be particularly effective. Chronic high rates of TEWL are believed to induce the release of critical skin growth factors such as interleukins and transforming growth factors resulting in a stimulation of dermis-epidermis growth and an angiogenic effect. Such treatments could be too severe for use on facial skin, but on thigh, arm and breast areas, which are prone to cellulite, the skin is more resistant. Treatment with the above composition thickens and improves the dermis and epidermis which hide cellulite, and the angiogenic effects improve long-term blood flow.

To obtain a further and more sustained elevation of TEWL, I have discovered that the addition of specific cerebrosides, Types I or II work synergistically with the above composition. The designations "I" and "II" can be understood to refer to particular molecular structures by referring to the structures of the corresponding ceramides, see for example Rieger et al. "Skin Constitutents as Cosmetic Ingredients" Cosmetic and Toiletries v. 107, pp 85–94, particularly, FIG. 2, page 88. In skin lipid metabolism, ceramides are produced by acylation of sphingosine and cerebrosides are the products of glycosylation of ceramides. Ceramides and cerebrosides make up a small percentage of skin lipids and are present in the outer layers of the skin, whereas sphingosine, their precursor, is found primarily in the basal layers. Sphingosine is also found in significant amounts in desquamated stratum corneum cells, as ceramides are enzymatically degraded during the exfoliation process.

The barrier-disruptive treatments of the invention release signals to the lower levels of the skin to increase synthesis of lipids such as ceramides and repair the barrier. A non-limiting hypothesis of the invention is that application of cerebrosides I or II may interfere with this synthesis, preventing the barrier from repairing itself. It is possible that a general inhibitor of lipid synthesis, or other end products of skin lipid synthesis, other than cerebrosides I or II, may also be effective supplements to the treatments described above to sustain elevated TEWL and thus promote skin repair over an extended period. In a recent paper Dr. Sergio Curri presented at a Cosmetic & Toiletry Convention in Barcelona, Spain, March 1994 Curri's he suggested that inhibition of protein kinase C, for example by sphingosine may be a useful cellulite treatment. This suggestion implies that cerebrosides would not be helpful in treating cellulite. In tests not reported here, I have found that phospholipids, ceramides and sphingosine have minimal effect as barrier repair inhibitors for the purposes of the present invention and I have further found that cerebrosides used alone are not useful in controlling TEWL or treating cellulite.

A further desirable and important function of a cellulite treatment is to reduce or eliminate the abnormal accumulations of subcutaneous fatty masses that are unpleasantly characteristic of cellulite. Pursuant to the objectives of this invention, a slow natural breakdown of accumulated fat in the skin can be achieved by stimulating lipid metabolism, for example, through an increase in the skin enzymes ATPase and protein kinase C.

I have surprising found that by incorporating cerebrosides in a topically applied cosmetic composition, lipid metabolism can be inhibited. While my invention is not limited by any particular theory, being limited only by the claims hereinbelow, it appears that cerebrosides have a very specific role in the regeneration of the stratum corneum barrier. When the barrier is impaired, specific signals are released, triggering an activation of epidermal and dermal metabolism. Some of these signals activate the synthesis of new epidermal lipids to repair the barrier and return TEWL to normal. This repair turns off signals responsible for activating epidermal and dermal metabolism (and for activating subcutaneous synthesis of new blood vessels). The addition of selected cerebrosides (but not ceramides nor sphingosine) interferes with the barrier repair to such a degree that the activation of epidermal and dermal metabolism is maintained over a long period of time resulting in changes which improve the cellulite condition. The barrier repair interference caused by selected cerebrosides is not such as to cause negative surface effects. Rather, it appears to be an interference with epidermal lipid production which enables activated epidermal and dermal metabolism to be maintained over extended periods of weeks and months. These concepts are verified by the results of clinical experiments reported hereinbelow These conclusions and results as to barrier repair inhibitor role for cerebrosides are quite unexpected since conventional teaching suggests that cerebrosides should repair a defective barrier.

I have concluded that the effects of cerebrosides are quite specific and are on the stratum corneum, but this is theory offered were by way of explanation to elucidate the mechanism of the invention of the invention as best I understand it. Future research by myself or other workers may suggest a different mechanism or mechanisms. It is possible that cerebrosides, through an action of protein kinase C, may also influence fat lipid metabolism directly in the subcutaneous regions.

When incorporated in topical treatments as described herein, the foregoing cerebroside ingredients work long-term, for example over 10 to 20 weeks, to improve skin quality, and the cellulite condition.

As is shown by experiments described and reported hereinbelow I have discovered that the combination of a TEWL elevator, in particular, lactic acid, with a retinoid, in particular vitamin A palmitate and a skin barrier repair inhibitor, in particular a cerebroside, preferably a type I or type II cerebroside, results in a sustained and chronic elevation of TEWL and disruption of barrier function, leading to the above-described, desirable skin repair and cellulite amelioration effects.

TEWL elevators: hydroxycarboxylic acids

Preferably, the TEWL elevator is soluble in water or a somewhat polar hydroalcoholic vehicle to provide an effective solution of the active ingredient for incorporation in cosmetic foundations. Many other alpha hydroxy acids can be used as alternatives to lactic acid. Lactic acid is a particularly preferred TEWL elevator in the practice of this invention, having excellent efficacy and being a naturally occurring substance found in skin and intercellular fluids as well as in the bloodstream. Some preferred alternatives to lactic acid are glycolic acid, salicylic acid and mixtures of these acids.

In order to have desired pH-reducing and TEWL-elevating properties as well as cosmetic compatibility and moderate water or hydroalcoholic solubility, preferred hydroxybenzoic acids have a molecular weight below about 250 and preferably below about 175.

Many useful hydroxycarboxylic acids are described in my International Patent Application WO/94/06440 which corresponds to U.S. Ser. No. 07/944,503, abandoned in favor of U.S. Ser. No. 08/214,032, now U.S. Pat. No. 5,520,918 dated May 28, 1996. Some additional alpha hydroxycarboxylic acids are described in Yu and Van Scott's U.S. Pat. Nos. 4,363,815 and 5,091,171. The acids and acid equivalents described in these publications, the disclosures of which are merely incorporated herein by reference thereto, can be employed in the practice of the present invention if they meet the criteria described above. Preferably, the alpha hydroxy acid used in my inventive composition is a straight or branched chain aliphatic acid with not more than three substituents in the aliphatic backbone, said substituents being non-basic and being selected from the group consisting of hydroxy, aldehyde, keto, carboxyl, chloro and nitro.

While acidity and water or hydroalcoholic solubility are desirable characteristics of the alpha hydroxy acids of the present invention, any extremes of these characteristics, such as would be displayed by a mineral acid, are undesirable as being liable to induce not just irritation but severe clinical conditions such as burning, lesions and sub-cutaneous penetration. Such undesired characteristics can sometimes be displayed by low molecular weight materials which may exhibit unusual and unpredictable, and often harmful, idiosyncratic behavior Such other alpha hydroxyaliphatic acids that can be used in practicing this invention are preferably monocarboxylic acids selected from the group consisting of 2-hydroxy-n-butanoic acid, 2-hydroxy-isobutanoic, 2-hydroxy-n-pentanoic, 2-hydroxy-isopentanoic, 2-hydroxy-n-hexanoic acid, 2-hydroxy-isohexanoic acid. Di-or polyhydric analogs thereof can also be used, for example, 2, X-dihydroxy analogs thereof where "X" is an integer from 3 to 6, as appropriate for the respective monohydroxy acid, indicating the carbon atom location of a second hydroxyl substituent in a carbon atom other than the one or two carbon atoms. Preferably, such dihydroxy acids balance the additional electronegativity attributable to the second hydroxyl with a further hydrophobic moiety as described above. Some examples of suitable dihydroxy acids are maleic acid, $(CH.COOH)_2$ and azelaic acid $HOOC.(CH_2)_7.COOH$.

Inhibitors of restoration of barrier function

In accordance with the invention, preferred inhibitors of restoration of barrier function are retinoids, for example tretinoin, or retinoic acid. However, many retinoids or retinoics are unstable and not suitable for marketing in a cosmetic topical treatment composition. Vitamin A palmitate is a particularly stable retinoid and is therefore preferred for use in this invention. Other stable retinoids suitable for formulating in compositions according to this invention include retinyl acetate and retinyl alcohol.

Other retinoids having a stable retinyl group linked to a fatty acid chain providing oil-stability and good solubility in the topical application vehicles described herein, can be used in the inventive compositions. In practicing the methods of the invention, shelf life may not be important.

Accordingly, stability of the selected retinoid may be less significant if, for example, topical applications are made up on an as-needed basis and are not stored for long periods, enabling less stable retinoids to be used.

Many active retinoids are known and believed in the practice of the present invention, for example, as listed in Kligman U.S. Pat. No. 5,051,449, the disclosure of which is hereby incorporated herein by reference thereto. Some other such retinoids are vitamin A aldehyde, vitamin A acid, vitamin A esters, isotretinoin, etretinate, acitretin retinoid esters, esters and amides of 13-cis and 13-trans-retinoic acid and retinyl glycosides.

Barrier Repair Inhibitor

As indicated above, cerebrosides have been found to fill a valuable functional role as barrier repair inhibitors for the purposes of this invention and this role is believed to be achieved by inhibiting the synthesis of lipids whose incorporation in the stratum corneum provides normal water barrier functions. In keeping with this concept, other substances are contemplated as filling the desired barrier repair inhibition role.

Cerebrosides for use in the practice of the invention are commercially available in several forms. They are sometimes supplied as glycosphingolipids (GSL) which term includes any lipid with a sphingosine group linked to a sugar. As supplied, cerebrosides are a principle component of GSL which are somewhat crude biological isolates from plants or animals. A relatively pure (99%) mixture of Types I and II bovine brain cerebrosides is available from Sigma Chemical Co., catalog number C 4905.

Relative proportions of ingredients

One limit on the strength of the cellulite treatment compositions of the invention is the degree of irritation they induce. Cellulite-afflicted areas are generally less sensitive than facial on which the skin treatment properties of some possible ingredients of the compositions of the invention have been demonstrated or tested in formulations such as "wrinkle" creams or anti-aging creams which work more than superficially to promote skin rejuvenation. Accordingly, because of the lower tissue sensitivity of cellulite-afflicted areas, preferred formulations of the novel cellulite treatment compositions employ higher proportions, or permit higher ranges of proportions of active ingredients than are used in skin creams intended for facial application.

Depending upon its potency and irritability, a useful proportion of TEWL elevator, preferably an alpha hydroxycarboxylic acid, for incorporation in a topical treatment composition is from 1 to 15 by weight of the composition, with a mid-range proportion of from 5 to 10 percent being preferred, especially for lactic or glycolic acid.

Where a retinoid is employed as a cell renewal stimulant, a useful proportion is from about 0.005 to about 6.0 percent by weight, with from about 1.0 to 4.0 percent being preferred although proportions in the range of from 0.1 to 1.0 can be expected to be active, albeit less effective.

When a cerebroside or a cerebroside mixture is used as the barrier repair inhibitor of the invention, a useful proportion of barrier repair inhibitor is from about 0.01 to about 5 percent with a range of from about 0.05 to about 1 percent being preferred and of from about 0.1 to about 0.5 percent being particularly preferred.

Unless otherwise stated, or apparent from the context, the proportions used herein are by weight based on the total weight of the composition and refer to the proportion of active ingredient or its equivalent.

PH of treatment compositions

Depending upon the acidity of the TEWL elevator a preferred pH is somewhat acidic, and indeed sustained moderate, but tolerable, acidity is believed to promote barrier disruption. Accordingly a preferred pH is in the range of about 3.0 to 6.2 with 4.5 to 5.5 being more preferred.

Optional Ingredients

Not essential, but an important optional feature of the invention, is the inclusion of an ingredient to improve the immediate appearance of cellulite. This can be achieved by immediately increasing blood flow and removing extraneous fluids. Known diuretic materials, such as caffeine, theophylline, methyl salicylate and other similar materials are quite effective. A preferred material is PRONALEN C (trademark, Centerchem, Inc.), a natural biological extract which can improve the initial acceptance of the product.

In general terms, useful optional additional ingredients, incorporated individually or in combination one with another, in cellulite treatment compositions according to the invention are diuretics, anti-irritants and anti-oxidants, preferably at concentrations known to be effective in topical cosmetics, for example from about 0.5 to 7.0 percent by weight, individually, and more preferably about 1 to 3 percent.

Diuretics promote lymphatic drainage and lipid catabolism and bring prompt short-term improvement to the cellulite condition that are apparent to the user. Examples of suitable diuretics are vasodilators, such as caffeine, xanthine and the like.

Anti-irritants and antioxidants can be used to optimize tolerance of sustained, elevated TEWL. Examples of suitable anti-irritants are kola extract, green tea, aloe, and the like and examples of suitable anti-oxidants are BHT, NDGA, vitamins E and C, and propyl gallate.

Inclusion of a combination of suitable optional ingredients provides a comprehensive, balanced cellulite treatment in which quick, readily apparent improvements are combined with long-term structural rectification of the condition, while irritation is also controlled.

Application Rates and Frequencies

Typical application rates of the inventive cellulite treatment compositions described herein can range from about 0.01 to 0.5 mg of active acid ingredients per square centimeter of skin, where the acid is a low-molecular weight hydrophilic acid, such as an alpha hydroxy carboxylic acid, with a range of from 0.05 to 0.2 mg/cm$^2$ being preferred. Cosmetic creams are generally applied at a rate of about 2–3 mg/cm$^2$. With an active ingredient proportion of about 0.15 to about 30 weight percent, this gives a possible rate of application of active ingredients of from about 0.003 mg/cm$^2$ to 0.9 mg/cm$^2$. A preferred range is from about 0.01 to 0.5 mg/cm$^2$ with a range of from 0 05 to 0 2 mg/cm$^2$ active ingredient per unit skin area being more preferred. Using a preferred proportion of about 7% active ingredients, in total, gives a preferred application rate of about 0.15 to 0.2 mg/cm$^2$.

This dosage is applied to whatever skin area requires treatment, preferably once or twice a day. More frequent applications of three or four times a day are likely to be wasteful of product without providing additional benefits, whereas less frequent applications, notably once a day, result in reduced efficacy. Additional applications may occasionally be made after washing, bathing or swimming, up to a maximum of about six times a day.

Alternative barrier disruption treatments

As an alternative to disrupting the water barrier with a combination of an alpha hydroxy acid and a retinoid, TEWL can be increased via stratum corneum stripping, solvent extraction and the like.

Acetone.

Daily, or every other day, rinses with acetone have also been found to disrupt the skin's water barrier, when continued over a long period of time, for example, two months. Biophysical measurements suggest that such an acetone rinsing regimen should deliver the above-described long-term skin-repair effects. Acetone will remove lipids as they are forming and interfere with barrier repair. Acetone is however, strongly irritating, flammable, and noxious and is not recommended for use. Data such as that reported in Table 2, help confirm that the broad scope of the concepts of the invention is not limited to application of cosmetic compositions to disrupt the skin water barrier and elevate TEWL but extends to other, physical and physico-chemical treatments.

Tape stripping.

Stripping the skin 5–10 times with adhesive-coated cellophane tape is another effective barrier disruption method which increases TEWL 2 to 10 times, varying according to an individual subject's particular response. Over an 8-week period this treatment can induce positive biological effects consistent with a useful cellulite therapy. Positive results with this treatment further confirm the broad technical scope of the invention. However, tape stripping has numerous drawbacks for use as a commercial process including but not limited to the fact that responses to tape stripping vary widely with different individuals, and an expensive, lab instrument must be used to monitor barrier function.

Surfactant stripping.

It has also been discovered that a strong aqueous surfactant solution used on a daily basis can disrupt the barrier chronically. A surfactant such as 10% sodium lauryl sulfate (SLS) applied twice a day is sufficient. Used alone, SLS is irritating to use over an 8-week period. Addition of 0.1% sphingosine may effectively control or reduce long-term irritation so that the treatment is considered mild enough to use as a practical embodiment of the invention. While anti-oxidants and immediate-effect anti-irritants such as kola nut extract may also be included, cerebrosides would not be incorporated in a composition containing sphingosine.

If desired, any of these or environment non-cream treatment, which are effective to elevate TEWL, can be accompanied by topical application of a cream containing a retinoid and, optionally, a cerebroside, to prolong TEWL elevation and skin repair processes.

Suitable vehicles

Any cosmetically acceptable vehicles customarily employed for delivering skin-renewal stimulating acids to the skin can be employed in the practice of this invention. Suitable vehicles may be aqueous, or hydroalcoholic, or employ oil or other hydrophobics in dispersions to provide common formulations into creams, lotions, tonics and the like. Creams are preferred for the topical treatments of this invention. If desired, the vehicle can simply be plain water, although small quantities of alcohol or other organic solvent may be needed to dissolve or disperse the small quantities of hydropholic retinoids and cerebrosides employed by the present invention.

If desired, the active ingredients can be formulated in a cosmetically acceptable hydroalcoholic vehicle having from about 40 to 75 weight percent of water, preferably 55 to 65 or about 60%, and from about 25 to 55 weight percent, preferably from about 25 to 35 or about 30 percent of an aliphatic alcohol. While a number of lower aliphatic alcohols, both monohydric and polyhydric can be used, ethanol and propanol are the most preferred choices. Many additives and supplemental materials are known to the art as being useful for incorporation in such vehicles, for example, glycerine up to about 5 percent, preferably 1 or 2 percent is useful as a humectant to counteract the drying effect of the alcohol and to improve the feel of the tonic. Stabilizers, fragrances and colorants are examples of other such additives.

Other suitable vehicles include a hydrophobic dispersion of from about 5 to about 60 weight percent of a hydrophobic fluid dispersed in an aqueous medium, and water.

If necessary, pH adjustment to an acceptable range can be effected with from 0.1 to 10 weight percent of an alkaline medium, for example aqueous sodium hydroxide, arginine or triethanolamine (TEA). Since the pH of the skin-renewal stimulating compositions of this invention has an important bearing on their efficacy, the presence of an appropriate buffer may also be desirable. Any such buffer or buffering system, acting in conjunction with the alkaline medium, should of course act to provide an acidic pH within the ranges described above, and preferably to keep the pH at 4.5 or below. The quantity of buffer will depend upon its strength but will usually be from about 0.1 to 10 weight percent, preferably about 1 or 2 percent. Some suitable buffers are TRIS (trimethylolaminomethane) buffers and phosphate buffers.

An example of a cream-based formulation of a topically applied structural cellulite treatment according to the invention will now be described.

| Novel three-component cellulite treatment in a cream vehicle The following ingredients are mixed according to the directions given below ("Concn." = concentration and the "Phase" number groups the ingredients for addition at different stages of the mixing process): | | |
|---|---|---|
| Ingredient | Concn. | Phase |
| Cetearyl alcohol (and) ceteareth-20 | 3.5 | 1 |
| GMS-PEG 100 stearate | 3.5 | 1 |
| PEG-100 stearate | 2.0 | 1 |
| dimethicone | 5 | 1 |
| squalene | 6 | 1 |
| capric triglyceride | 4 | 1 |
| propylparaben | 0.1 | 1 |
| vitamin A palmitate | 1.5 | 1 |
| water | 45 | 2 |
| glycerine | 5 | 2 |
| butylene glycol | 6 | 2 |
| carbomer 941 | 0.2 | 2 |
| methyl paraben | 0.25 | 2 |
| triethanolamine | 3.1 | 3 |
| lactic acid | 8 | 4 |
| cerebrosides 1 & 2 | 0.15 | 5 |
| pronalen AC (Centerchem) | 5 | 6 |
| fragrance | QS | 7 |
| water | QS to 100% | — |

Those skilled in the art will be familiar with methods for formulating these ingredients into a smooth cream for topical application. The oil phase (1) is slowly added to phase (2) at 80° C. with mixing. After the resultant emulsion begins to form phase (3) is added and the cream thickens. Next phase (4) is added and phase (5–7) ingredients are added as the cream cools to 55° C. It is then cooled to room temp with mixing.

In this Example it will be apparent that vitamin A palmitate, lactic acid and cerebrosides I and II are active ingredients according to the invention while the balance of ingredients constitutes a cream vehicle.

Clinical Experiments with Novel Cellulite Treatments

The results of clinical experiments with novel cellulite treatments are reported in Table 2 below. Treatments 2.1 to 2.4 were conducted using the cream vehicle described in the Example above, with the active ingredients and proportions reported in the Table. Treatments 2.1 to 2.3 and 2.5 may be novel, but are for comparative purposes and are not preferred embodiments of the invention.

TABLE 2

| | Cellulite treatments according to the invention | | | | | | | |
|---|---|---|---|---|---|---|---|---|
| Treatment | Blood flow | TEWL g/m2/hr | TEWL incr. % | Firm | Thigh Diam. | Skin Thickness | Cell. | Irrit. |
| 2.1) 5% lactic acid | | | | | | | | |
| bl | 1 | 2.07 | | x | x | x | 4.25 | 1 |
| 8 wks | x | 2.33 | 13 | x | x | x | 4 | 1.5 |
| 12 wks | 1.11 | 2.47 | 19 | 27% | −3% | 7%(ns) | 3.75 | 1.5 |

TABLE 2-continued

Cellulite treatments according to the invention

| Treatment | Blood flow | TEWL g/m2/hr | TEWL incr. % | Firm | Thigh Diam. | Skin Thickness | Cell. | Irrit. |
|---|---|---|---|---|---|---|---|---|
| 2.2) 10% lactic acid | | | | | | | | |
| bl | 1 | 2.11 | | x | x | x | 4.25 | 1 |
| 8 wks | x | 2.69 | 27 | x | x | x | 3.5 | 1.5 |
| 12 wks | 1.07 | 2.83 | 34 | 30% | −1% | 10%(ns) | 3 | 2 |
| 2.3) 10% LA/1% VAP | | | | | | | | |
| bl | 1 | 2.03 | | x | x | x | 4.25 | 1 |
| 8 wks | x | 3.47 | 71 | x | x | x | 3.5 | 2 |
| 12 wks | 1.12 | 3.67 | 81 | 29% | −5% | 8%(−4%) | 2.75 | 2.5 |
| 2.4) 10% LA/1% VAP/0.5% GSL | | | | | | | | |
| | 1 | 1.91 | | x | x | x | 4.25 | 1 |
| bl | x | 3.87 | 102 | x | x | x | 2.75 | 2 |
| 8 wks | 1.43 | 6.88 | 260 | 43% | −11% | 10%(−8%) | 2 | 2.5 |
| 12 wks | | | | | | | | |
| 2.5) daily 2x BUFF PUFF tm | 1 | 2.14 | | x | x | x | 4.25 | 1 |
| bl | x | 2.39 | 8 | x | x | x | 4 | 1.5 |
| 8 wks | 1.07 | 2.31 | 8 | 6% | 2% | ns(ns) | 3.75 | 2 |
| 12 wks | | | | | | | | |
| 2.6) daily 5–10x stripping | 1 | 2.14 | | x | x | x | 4.25 | 1 |
| bl | x | 5.37 | 151 | 11% | x | 6%(ns) | 3.75 | 2.5 |
| 8 wks | 1.17 | 6.07 | 184 | 17% | −8% | 10%(−5%) | 3 | 3 |
| 12 wks | | | | | | | | |
| 2.7) acetone washes (every 2 days) | 1 | 2.17 | | x | x | x | 4 | 1 |
| bl | 1.12 | 6.92 | 219 | 7% | −3% | 6%(3%) | 3 | 2.75 |
| 8 wks | x | x | | x | x | x | x | x |
| 12 wks | | | | | | | | | bl = baseline. LA = lactic acid. VAP = vitamin A palmitate. GSL = glycosphingolipid
ns = not significant Referring to Table 2, somewhat greater TEWL elevations were obtained with treatments 2.1 and 2.2 employing lactic acid, but even the level for the strong exfoliating 10% lactic acid composition of treatment 2.2 is only about 33% Higher levels are desirable to obtain the benefits of this invention. Treatment 2.3 with vitamin A palmitate added to lactic acid shows a TEWL elevation at 8 weeks of about 71% and at 12 weeks of about 81%. Although these elevations of TEWL are more substantial than those obtained with known treatments, the inventive barrier disruption treatments 2.4, 2.6 and 2.7 achieve much higher elevations of TEWL and ranged from over 100% to as much as 260%. Irritation levels, although elevated somewhat, remained tolerable.

Basal blood flow as reported in column 1, showed a modest response to all treatments except treatment 1.1 (Table 1) employing retinoic acid which shows a 27% increase at 12 weeks, and more strikingly, treatment 2.4 employing a preferred topically absorbed treatment according to the invention, shows a much higher basal blood flow increase of about 43% at 12 weeks.

With regard to the general cellulite condition graded in the next to last right-hand column, the apparent improvements reported for treatments 1.2 to 1.6, treatment 2.1 and treatment 2.5 are either not significant or very modest. A modest improvement is obtained with treatment 1.1 retinoic acid at 12 weeks which shows a decline of 1 grading point. whereas treatments 2.2, 2.3, 2.4 and 2.6 all show improvements of greater than 1 point with the preferred inventive embodiment of 2.4 showing an improvement in excess of 2 grading points. Acetone wash treatment 2.7, shows an improvement of 1 point confirming the concept of the invention.

A grading for clinical irritation is shown as a safe guard. Excessively irritating treatments are unacceptable. An irritation grading approaching 3 begins to be undesirable and it may be noted that the acetone wash treatment, treatment 2.7, not surprisingly, shows a significant irritation level of 2.75 at only 8 weeks whereas, the preferred low-irritant embodiment of treatment 2.4 shows an irritation rated at only 2.

Thigh firmness was improved significantly (near 30%) by lactic acid (treatments 2.1 and 2.2) with no further improvement when a retinoid (VAP) was included (treatment 2.3). Adding cerebroside-containing glycosphingolipids, pursuant to the invention (treatment 2.4) achieved a significant further increase to 43%, indicating pronounced structural improvements in the condition of the underlying tissues. Stripping (treatment 2.6) shows more modest improvements while "BUFF-PUFF" and acetone washing (treatments 6.5 and 6.7) show insignificant improvements in firmness.

Thigh diameter is significantly reduced by the preferred 2.4 treatment, to a lesser extent by acetone washing (treatment 2.6) and not significantly, or only marginally by other treatments.

While treatments 2.1–2.4 and 2.6 all showed some improvement in epidermal-dermal skin thickness, first figure, only the inventive treatments 2.3, 2.4 and 2.6 show reductions in the thickness of the subcutaneous region, parenthetically. The preferred 2.4 treatment shows substantially the best results in both categories.

In summary, the data reported in Table 2 show that the inventive treatments 2.3, 2.4, 2.6 and 2.7 provide much greater TEWL elevations than comparative treatments and these elevations are accompanied by improvements in blood flow and skin structure not obtained by comparative treatments. The preferred inventive composition of treatment 2.4 shows far and away the best results with marked TEWL elevations accompanied by major blood flow improvements and significant macrostructural and microstructural skin and deeper tissue improvements.

To evaluate microcirculatory improvements, detailed blood flow studies were carried out employing ultrasound analysis as described above with the results reported in Tables 3–6 below.

TABLE 3

Microcirculation determined by laser doppler shifts
Effects of test composition on normal skin
Blood flow rates
Summary of results on 5 subjects, 10 measurements on the forearm of each subject.
Blood flow Measurements

| Test Group | less than 1 | between 1–3 | between 3–5 | between 5–7 | >7 |
|---|---|---|---|---|---|
| Before | 3 | 11 | 22 | 10 | 4 |
| After 8 wks | 1 | 9 | 20 | 14 | 6 |
| After 16 wks | 0 | 5 | 21 | 17 | 7 |
| Irritant | 0 | 0 | 0 | 3 | 47 |

The blood flow measurement results shown in Table 3 are reported in arbitrary relative numbers. Of a total of 50 points of measurement, it may be seen, in the last line of Table 3 that the control irritant stimulated a blood flow in excess of 7 for almost all measurement points, namely 47 of the 50. Reading down the table, as the time scale advances from initial readings to those after 8 and 16 weeks of treatment with the test cellulite treatment composition, so the number of readings in each group moves to the right. This shows that applications of the test composition result in a substantial increase in the number of higher blood flow measurements.

Whereas the number of blood flow readings in the center column (having a value between 3 and 5) remains approximately constant, those below 3 (summing the number of measurements in columns 1 and 2) declines from an initial 14, to 10 at 8 weeks, and to 5 after 16 weeks. Referring to the two right-hand columns, it may be seen that the number of measurements over 5 is only 14 before the treatment, but rises to 20 at 8 weeks, and to 24 after 16 weeks. Overall, the numbers shift to the right, with time, as blood flow improves. Thus, Table 3 shows that the applied cellulite treatment composition is effective to provide a significant stimulation of blood flow at 8 weeks and that continued application of the treatment composition provides a sustained increase of blood flow, showing further improvements at 16 weeks.

As noted, the Table 3 determinations were made on the forearms of subjects with normal, cellulite-free skin. This data gives a clear picture of the blood flow stimulating characteristics of the topically applied composition, while eliminating complications arising from the abnormalities of structures in cellulite-afflicted tissues.

TABLE 4

Microcirculation by laser Doppler shift
Thigh area circulatory problems
Blood flow rates
Summary of results on 10 subjects: All showing signs of cellulite stages 2/3. 30 measurements on each subject.

| Test Group | less than 1 | between 1–3 | between 3–5 | between 5–7 | >7 |
|---|---|---|---|---|---|
| Before | 68 | 133 | 42 | 43 | 14 |
| After 8 wks | 45 | 123 | 67 | 52 | 13 |
| After 16 wks | 17 | 67 | 128 | 71 | 17 |
| Control-uninvolved | 6 | 51 | 128 | 110 | 5 |

Reference Data:
The control group had an average age of 23.6 years
Application of a known irritant such as Balsam of Peru increased blood flow rates to 10–12 in this test method.

Table 4 reports the results of measurements at a total of 300 thigh area points on 10 subjects having advanced cellulite, meeting the criteria of cellulite stages 2 or 3, as described above. The bottom line readings are control measurements on skin areas uninvolved with cellulite. The Table 4 data can be read in the same way as Table 3. Of particular note are the figures in the first column, which show a large number of measurement areas exhibiting very poor blood flow rates below a value of 1 as a result of their cellulite condition, whereas only 6 measurements of the uninvolved group were below 1.

Topical application of the test cellulite treatment composition of the invention was effective in reducing the number of measurement points below 1 from 68, before treatment, to 45 at 8 weeks, and to 17 after 16 weeks of treatment. The numbers show a general shift to the right at 8 weeks and a still further shift at 16 weeks, demonstrating a continual improvement in blood flow, attributable to the beneficial effects of the tested cellulite treatment composition.

TABLE 5

Microcirculation by laser Doppler shift
Thigh area circulatory problems
Blood flow rates

| Subject #1 Stage 2/3 Cellulite | | Age 46 Before Treatment | | |
|---|---|---|---|---|
| 1.04 | 1.22 | 4.67 | 4.56 | 1.11 |
| 2.45 | 0.45 | 0.56 | 2.67 | 0.98 |
| 2.22 | 0.67 | 0.67 | 3.55 | 0.76 |
| 0.67 | 2.19 | 0.78 | 2.78 | 3.67 |
| 0.78 | 3.11 | 0.88 | 2.55 | 3.56 |
| 2.67 | 3.42 | 5.6 | 8.89 | 5.66 |

| Subject #1 Stage 2/3 Cellulite | | Age 46 After 16 week Treatment | | |
|---|---|---|---|---|
| 1.33 | 1.92 | 5.11 | 5.03 | 1.44 |
| 2.55 | 1.59 | 2.56 | 3.03 | 1.22 |
| 2.78 | 2.22 | 3.12 | 4.03 | 1.33 |
| 1.87 | 2.45 | 1.44 | 3.11 | 3.99 |
| 1.12 | 3.84 | 1.09 | 2.77 | 4.03 |
| 3.04 | 4.30 | 6.15 | 6.89 | 5.88 |

Table 5 reports a detailed study of the effect of the inventive cellulite composition on single subject. The relative blood flow measurements are reported to two significant figures. Comparative measurements were made at 30 different positions on the subject, reporting readings before treatment in the upper half of the table, and readings after 16 weeks of treatment in the lower half of the table. Thus, a reading in any particular position in the upper half of the table can be compared with a reading in the saved relative position in the lower half of the table to determine the impact of the tested treatment composition, as in "before" and "after" comparison.

With one exception, all readings improve after treatment. The exception is the anomalously high 8.89 reading. This can be attributed to poor blood flow in adjacent areas. All the readings below 1 are improved to a value above 1, some of them quite dramatically. Thus the third reading in column 2, improves from 0.67 before treatment to 2.22 after treatment. Again, Table 5 shows a highly significant overall improvement in blood flow over a wide area of the cellulite-afflicted thighs of a single subject, attributable to structural microcirculatory vasculative improvements caused by the inventive treatments.

TABLE 6

Ultrasound analysis of skin thickness
Averages of results on 10 subjects, measurements on the thigh of each subject.

| Test Group | Epi/Derm Thickness | Epi/Derm Density | Subcut Thickness | Subcut Density |
|---|---|---|---|---|
| Before | 2.34 | 68% | 4.12 | 33% |
| After 8 wks | 2.56 | 74% | 3.99 | 41% |
| After 16 wks | 3.12 | 82% | 3.25 | 62% |

Table 6 shows that after 8 weeks of treatment, both the epidermal-dermal skin layers increase in thickness and the subcutaneous skin regions show reductions. Both show significant density increases. Further significant improvements are obtained after 16 weeks of treatment with the applied composition. These data suggest that the compositions of the invention provide significant structural improvements in skin condition which can lead to long-term benefits in cellulite conditions.

INDUSTRIAL APPLICABILITY

The present invention is particularly suitable for application in the cosmetics industry to provide new formulations and methods of cellulite and skin treatment.

While an illustrative embodiment of the invention has been described above, it is, of course, understood that various modifications will be apparent to those of ordinary skill in the art. Such modifications are within the spirit and scope of the invention, which is limited and defined only by the appended claims.

I claim:

1. A method of ameliorating a cellulite condition comprising application of a topical treatment composition to skin areas overlying cellulite, said treatment composition being effective to chronically disrupt the barrier function of the stratum corneum and to inhibit barrier repair until a desired amelioration of cellulite is achieved.

2. A method according to claim 1 wherein said treatment is continued for at least eight weeks.

3. A method according to claim 1 wherein said treatment is effective to elevate trans-epidermal water loss by at least one hundred percent and said period of time is at least from eight to twenty-six weeks.

4. A method according to claim 1 wherein said treatment comprises topical application of a cosmetic composition comprising, in proportions based on the weight of the composition:

a) a cosmetically compatible, pH-reducing, hydroxycarboxylic acid in a proportion of from about 1 to about 15 percent;

b) a retinoid cell renewal stimulant in a proportion of from about 0.0005 to about 6 percent; and c) a cerebroside barrier repair inhibitor in a proportion of from about 0.01 to about 5 percent.

5. A method according to claim 4 wherein said cosmetic composition is topically applied twice daily for at least eight weeks.

6. A method according to claim 4 wherein the hydroxycarboxylic acid comprises from about 5 to about 10 percent of lactic, glycolic or salicylic acid, the retinoid cell renewal stimulant comprises from about 0.3 to 3 percent of vitamin A palmirate and the cerebroside barrier repair inhibitor comprises from about 0.1 to about 0.5 percent of a cerebroside material.

7. A method of ameliorating a cellulite condition comprising application of a topical treatment to skin areas overlying cellulite, said treatment being effective to disrupt the water barrier function of the stratum corneum and to induce chronic elevated trans-epidermal water loss for period of from eight weeks until a desired amelioration of cellulite is achieved, wherein said treatment is selected from the group of skin water barrier disruption treatments consisting of application of exfoliants in solution, mechanical abrasion and solvent extraction of hydrophobic skin barrier components.

8. A cellulite treatment composition for topical application to cellulite-afflicted skin areas, said composition being effective to disrupt the barrier function of the stratum corneum comprising, in proportions based on the weight of the composition:

a) a cosmetically compatible, pH-reducing, hydroxycarboxylic acid in a proportion of from about 1 to about 15 percent;

b) a retinoid cell renewal stimulant in a proportion of from about 0.005 to about 6 percent; and c) a cerebroside barrier repair inhibitor to inhibit repair of the skin's water barrier in a proportion of from about 0.01 to about 5 percent.

9. A cellulite treatment composition according to claim 8 wherein the hydroxycarboxylic acid comprises from about 5 to about 10 percent of lactic, glycolic or salicylic acid, the retinoid cell renewal stimulant comprises from about 0.3 to 3 percent of vitamin A palmitate and the cerebroside barrier repair inhibitor comprises from about 0.1 to about 0.5 percent of a cerebroside material.

10. A cellulite treatment composition according to claim 8 comprising at least one optional ingredient selected from the group consisting of diuretics to stimulate blood flow, anti-irritants and anti-oxidants to control irritation induced by disruption of the barrier function of the stratum corneum or by said cell renewal stimulant, and mixtures thereof.

11. A cellulite treatment composition comprising an agent to disrupt the barrier function of the stratum corneum, a cell renewal stimulant and a barrier repair inhibitor to inhibit repair of the skin's water barrier.

12. A cellulite treatment composition according to claim 11 wherein said barrier repair inhibitor is a cerebroside I or II, or a mixture thereof in a proportion of from about 0.01 to about 5 percent by weight.

13. A cellulite treatment composition according to claim 11 comprising at least one optional ingredient selected from the group consisting of diuretics to stimulate blood flow, anti-irritants and anti-oxidants to control irritation induced by said agent to disrupt the barrier function of the stratum corneum or by said cell renewal stimulant, and mixtures thereof.

14. A cellulite treatment composition according to claim 11 comprising from 5 to 10 percent lactic acid, from 0.5 to 4.0 percent vitamin A palmirate and from 0.1 to 0.5 percent cerebroside I or II or a mixture thereof.

15. A cellulite treatment composition according to claim 11 effective to elevate trans-epidermal water loss by at least 100 percent after eight weeks of application.

* * * * *